United States Patent [19]

Holly

[11] 4,241,721
[45] Dec. 30, 1980

[54] BODY WARMER

[76] Inventor: Gordon L. Holly, Rte. 1 Box 147, Hillman, Mich. 49746

[21] Appl. No.: 130,826

[22] Filed: Mar. 17, 1980

[51] Int. Cl.$^3$ ................................................ A61F 7/06
[52] U.S. Cl. .................................... 126/204; 126/206; 126/208; 2/69
[58] Field of Search ............... 126/400, 204, 206, 208; 165/46; 219/211; 2/69, 211, 216, 311; 138/103, 108, 119

[56] References Cited

U.S. PATENT DOCUMENTS

| | | | |
|---|---|---|---|
| 554,121 | 2/1896 | Harmer | 126/208 |
| 586,998 | 7/1897 | Harmer | 126/206 |
| 2,292,600 | 8/1942 | Baum | 2/69 |
| 2,346,998 | 4/1944 | Reveno | 126/204 |
| 2,459,352 | 1/1949 | Williams | 2/69 |
| 2,705,325 | 4/1955 | Bogenberger | 2/69 |
| 2,851,573 | 9/1958 | Muccilli | 126/204 X |
| 3,329,971 | 7/1967 | Shelby | 2/69 |
| 3,443,066 | 5/1969 | Weibel | 219/211 X |

FOREIGN PATENT DOCUMENTS 352866  5/1922  Fed. Rep. of Germany ........... 126/204

*Primary Examiner*—Samuel Scott
*Assistant Examiner*—Randall L. Green
*Attorney, Agent, or Firm*—Michael L. Bauchan

[57] ABSTRACT

A body warmer is provided that includes a platform, a heat source, an envelope surrounding the user, and hoops in the envelope. The envelope is kept from contacting the heat source by the hoops. The user is kept from contacting the heat source by a shield. The heat source is pivotally connected to the platform and movable from a first position in which it is stored to a second position in which it is used. A cushion is attached to the inside of a cover that seals the body warmer for storage.

11 Claims, 6 Drawing Figures

BODY WARMER

BACKGROUND OF THE INVENTION

This invention pertains to a body warmer which is portable and suitable for use by sportsmen and spectators and is also useful as a survival unit.

The broad concept of providing a relatively small envelope in which a person is positioned next to a heat source has been known for many years. For example, a U.S. Pat. No. 554,121 was issued Feb. 4, 1896 to G. W. Harmer utilizing a combination envelope and heat source in the form of a lantern. On Apr. 18, 1944 a U.S. Pat. No. 2,346,998 was issued to R. R. Reveno pertaining to a portable body warmer in which a chemical heat source is positioned in an envelope below the user's feet.

Sportsmen have need of a suitable body warmer, particularly when engaged in activities such as deer hunting, in which they sit in one position for a lengthy period. Spectators at various outdoor events also have need of a body warmer as even in relatively mild weather an inactive spectator can become quite cold. In addition, any person who becomes chilled, whether they are a lost hunter or a spectator or engaged in other activity, has need of a suitable body warmer to avoid the effects of hypothermia.

To be effective, most body warmers rely upon trapping a heated volume of air against the user's body. Since a body warmer intended to be portable must be lightweight and not bulky, such body warmers are not wall insulated and thus relay upon a relatively hot heat source.

The most effective body warmer is therefore one which permits entrapment of a relatively large volume of air around the body of the user to distribute heat from a hot source on the user's body and which also provides reasonable means for reducing likelihood that the user may come into actual contact with the heat source to reduce likelihood that the user or the user's apparel may be burned.

It is therefore an object of this invention to provide a body warmer which incorporates hoops and an envelope around the user to prevent the envelope contacting the heat source and to permit a desired air circulation within the envelope enclosure.

It is a further object of this invention to provide a body warmer which utilizes an envelope supported by hoops and a heat source proximate the user's feet which is shielded to prevent contact with the user and his apparel.

It is a further object of this invention to provide a body warmer in which the user may collapse the envelope and pivot the heat source into a convenient package for carrying on shoulder straps.

It is a further object of this invention to provide a body warmer having a pivoted heat source, a hoop supported envelope, and a cushion attached to a cover, all of which may be carried on shoulder straps.

It is a further object of this invention to provide a portable body warmer having a hoop supported envelope which is supported on the user by means of shoulder straps and which is sealed to the user by a drawstring.

SUMMARY OF THE INVENTION

This invention is of a unique portable body warmer incorporating a hoop supported envelope around a shield protected heat source. The envelope is supported on the user by shoulder straps and sealed to the user by a drawstring. A pivoted heat source is provided that may be placed in a storage position when the envelope is collapsed to permit a cushion containing cover to seal the apparatus for convenient carrying on shoulder straps attached to the base of the unit.

DISCUSSION OF THE DRAWINGS

This invention will be better understood from the accompanying description in conjunction with the accompanying drawings, in which.

DESCRIPTION OF THE PREFERRED EMBODIMENT

Figure 1:
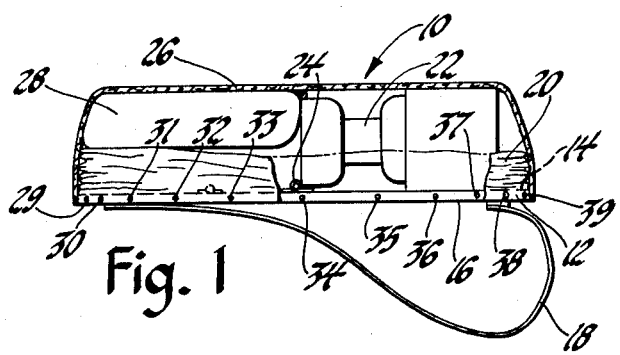
FIG. 1 is a sectional view of a body warmer incorporating the principles of the subject invention.

As shown in FIG. 1, a body warmer 10 includes a base 12 which forms a platform on which the user may stand. In the illustrated embodiment, the base 12 has a top surface 14 and a bottom surface 16. For convenient carrying, a pair of shoulder straps 18 is attached to the bottom surface 16 of the base 12.

An envelope 20 is attached to the top surface 14 of the base 12. A heat source 22 in FIG. 1 is pivotally attached to the top surface 14 of the base 12 by a hinge 24. Many common portable heat sources use kerosene or lantern fuel so for convenience the heat source will be called a lantern. A flexible cover 26 to which is attached a cushion 28 is illustrated in FIG. 1 as being connected by means of several snap fasteners 29 through 39 to the base 12.

Figure 2:
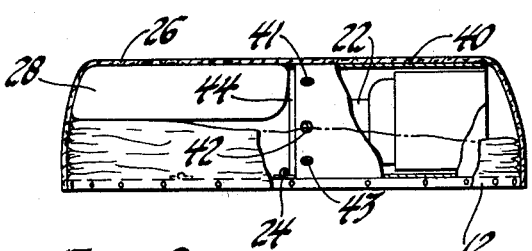
FIG. 2 is a sectional view of a body warmer of FIG. 1 provided with a heat shield.

As shown in FIG. 2, in the preferred embodiment the lantern 22 is positioned in a heat shield 40 having three air openings 41 through 43 to provide a suitable draft for the lantern 22. Persons versed in the art will appreciate that additional openings for a lantern draft may be provided. In the embodiment illustrated in FIG. 2, the heat shield 40 is attached to a support 44 that is pivotally mounted on the hinge 24 and the lantern 22 is rigidly secured to the support 44.

Persons versed in the art will appreciate that the heat shield 40 may be of many suitable materials, its primary function being to isolate the lantern 22 from the user and the apparel of the user so as to prevent either burning the user or the user's apparel. As such the heat shield 40 may be made of sheet metal or a screen and may either completely enclose the lantern 22 or may have an open end at the top of the lantern 22.

Figure 3:
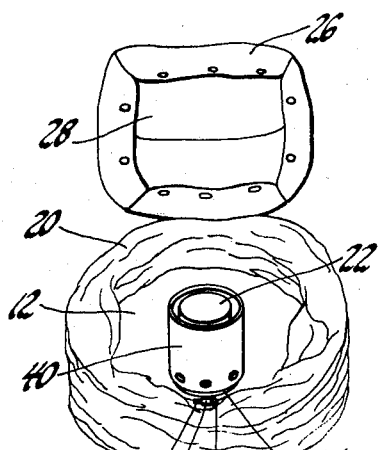
FIG. 3 is a perspective view of the body warmer in FIG. 2 with a heat source upright.

As shown in FIG. 3, the lantern 22 may be moved from the first position illustrated in FIGS. 1 and 2 to a second position in which the lantern 22 stands upright on the base 12. A latch 46 is provided that includes a bolt 48 rigidly secured to the base 12 and an eye 50 rigidly secured to the support 44. The latch 46 prevents accidentally tipping over the lantern 22.

Figure 4:
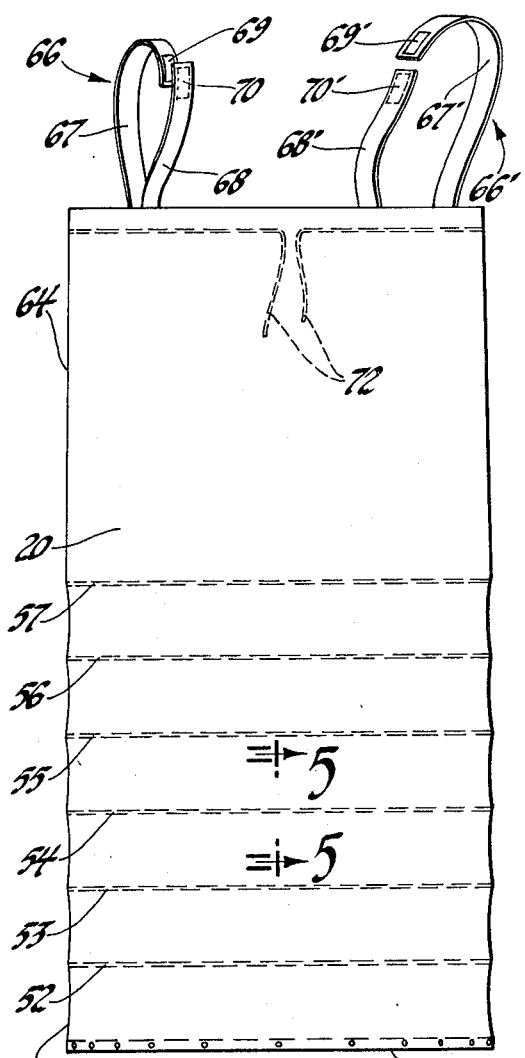
FIG. 4 is a perspective view of the body warmer in FIG. 3 with the envelope expanded for use.

As shown in FIG. 4, the envelope 20 is a flexible material fastened to the base 12 so as to form a substantially tubular configuration. While the envelope 20 in the illustrated embodiment is cylindrical, persons versed in the art will appreciate that it may be conical or of other configuration enclosures.

Figure 5:
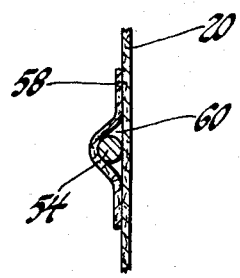
FIG. 5 is a partial sectional view of a hoop along the lines 5—5 in FIG. 4.

Several hoops 52 through 57 are attached to the envelope 20 to provide a measure of rigidity to the envelope 20 when it is moved upright. As shown in FIG. 5, the hoop 54 is attached to the envelope 20 by a material strip 58 that forms an opening 60 in which the hoop 54 is positioned. Each of the other hoops 52 through 57 are attached to the envelope 20 in a similar manner.

As persons versed in the art will appreciate, the functions of the hoops 52 through 57 include holding the envelope 20 away from the lantern 22 and also providing suitable air volume inside the envelope 20 to permit the high intensity heat of the lantern 22 to be distributed around the various surfaces of the user. The hoops 52 through 57 thus help avoid the envelope 20 resting directly on the user and thus having a great deal of heat in the vicinity of the lantern 22, which is at the lower end 62 of the envelope 20, while permitting the heat going from the lantern 22 to the upper end 64 of the envelope 20.

As shown in FIG. 4, the upper end 64 of the envelope 20 includes a first shoulder strap 66 having a first end 67 and a second end 68 which are provided with velcro strips 69 and 70. The velcro strips 69 and 70 permit attaching the end 67 and 68 in many positions to adjust the length of the shoulder strap 66. A second shoulder strap 66' is provided identical to the first shoulder strap 66 with corresponding first end 67' and second end 68' and velcro strip 69' and 70'.

The shoulder strap 66 and 66' thus provide a convenient and readily adjustable mechanism for supporting the envelope 20 on the user.

As shown in FIG. 4, a drawstring 72 is also provided on the inside of the envelope 20 at the upper end 64. The drawstring is sewn into a suitable opening formed in a manner similar to the opening 60 and may be tied inside the envelope 20.

Figure 6:
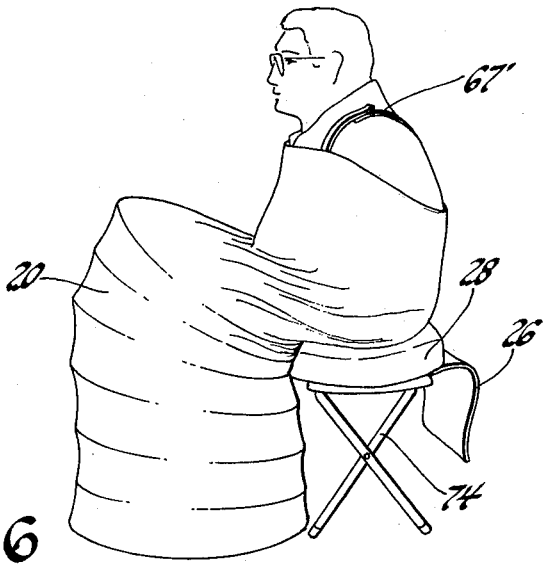
FIG. 6 is a perspective view of the body warmer in FIG. 3 in use.

Use of the subject body warmer as shown in FIG. 6 will now be explained.

For convenient storage and carrying, the body warmer is in a single package as illustrated in FIG. 1 and FIG. 2 and may be carried by the user slipping arms into the shoulder straps 18 on the bottom surface 16 of the base 12. The shoulder straps 18 are particularly useful in those instances where the user may be a hunter carrying game or weapons in his hands and thus needs to have his hands free.

When the user is in the desired position, he removes the cover 26 from the base 12 by unsnapping snap fasteners 29 through 39. He tilts the heat source lantern 22 to an upright position as shown in FIG. 3 and securely latches it in the upright position by sliding the bolt 48 into the eye 50.

The user then starts the heat source by lighting the lantern 22 and steps onto the base 12 so both of the user's feet are proximate the lantern 22. The user then pulls up the upper end 64 of the envelope 20 to a convenient height and fastens to it his shoulders by means of the shoulder strap 66 and 66'. The user then seals the upper end 64 of the envelope 20 by pulling the drawstring 72 and tying it to provide the desired amount of air flow from inside the envelope 20 to the atmosphere.

As shown in FIG. 6, the user may sit down while in the envelope 20 and thus utilize the convenience of the cushion 28 by placing it on a stool 74 or other object.

If the user is in relatively mild weather, he may elect to extend his arms outside the envelope 20 and loosen the drawstring 72 so as to permit more of the heated air from inside the envelope 20 to pass to the atmosphere. The envelope 20 in the illustrated embodiment is made of a suitable length so the user could let a firearm or other weapon rest on his lap while sitting and then raise the firearm when he stands and may fire his weapon without the necessity of removing the envelope 20 from his body.

It is thus apparent that the subject apparatus provides a very useful body warmer which can warm the entire body of the user, even including his arms inside the body warmer in cold weather. The shoulder strap 66 and 66' may easily be operated by cold fingers of the user due to the convenient velcro fasteners. In addition, the built in cushion 28 attached to the inside of the cover 26 provides comfort to the user.

When the user finishes use of the subject body warmer, he collapses the envelope 20 to the position illustrated in FIG. 3, turns off the lantarn 22, pivots the lantern 22 from the upright position to the first position for storage, and replaces the cover 26 on the base 12.

In the illustrated embodiment, the envelope 20 is shown as a flexible material. A fire retardant chemically treated canvas or other similar material would be most appropriate.

While in the illustrated embodiment the heat shield 40 is shown as being a separate entity, persons versed in the art will appreciate that the heat shield 40 may be part of the lantern 22 or other heat source which is utilized. It makes no difference whether the heat shield 40 is separate or is part of the heat source structure.

In practice, a portable heat source manufactured by the Coleman Manufacturing Company, which makes various heaters and lanterns, has proven to be a suitable heat source, but persons versed in the art will appreciate that many other types and manufacturers may be employed to provide a suitable heat source.

Persons versed in the art will appreciate that the base 12 may be of wood or plastic or metal, depending on manufacturing and price considerations. Similarly, the hoops 54 may be of metal or plastic or a wood such as bamboo.

Persons versed in the art will appreciate that various other modifications of structure and components may be made without departing from the spirit of the subject invention. For example, even though the hoops 52 through 57 in the illustrated embodiment are of substantially the same size and concentric it may be preferred to have them concentric but of different diameters to faciliate storage of same.

What is claimed is:

1. A body warmer to keep a person warm comprising, in combination, a platform having top and bottom surfaces and being substantially defined by a plane; a heat source secured to said platform so said person may stand on said platform top surface with each of said person's feet proximate said heat source; an envelope having an upper end and a lower end secured to said platform, said envelope being adapted to substantially surround the body of a person standing on said platform; at least one hoop secured to said envelope for preventing said envelope from contacting said heat source and for providing air circulation around a person in said envelope, said hoop being defined by a plane substantially parallel to the plane of said platform, thereby permitting said envelope to be collapsed onto said top platform surface around said heat source for storage; a shield substantially surrounding said heat source for preventing a person in said envelope from contacting said heat source; closure apparatus attached to said envelope upper end for supporting said envelope on said person in said envelope and for sealing said envelope against said person; and a cover having top and bottom surfaces and connection means for attaching said cover to said platform so said top platform surface faces said bottom cover surface whereby said heat source, said shield, and said envelope may be stored between said cover and said platform and said cover may be securely attached to said platform by said connection means.

2. The body warmer of claim 1 in combination with two shoulder straps attached to the bottom surface of said platform whereby said body warmer may be carried on the shoulders of said person when said cover is attached to said platform.

3. The body warmer of claim 1 in which said heat source is a fuel consuming lantern and said shield is rigidly attached to said lantern and is pivotally attached to said top platform surface and a latch mechanism is attached to said top platform surface whereby said heat source and shield may be placed in a first position between said cover and said platform for storage and may be pivoted to a second position for use and said latch may securely retain said heat source and shield in said second position during use so as to prevent said heat source accidentally being dislodged from said second position.

4. The body warmer of claim 1 in which said closure apparatus is comprised of at least one shoulder strap having two ends that are each attached to said upper envelope end for supporting said envelope on the shoulder of said person while said person is in said envelope and a drawstring in said upper envelope end for selectively sealing said envelope to said person to adjust the amount of air circulation from said envelope to the atmosphere.

5. The apparatus of claim 1 in the combination with a cushion on said bottom cover surface whereby said cover may be used as a cushion on which said person may sit while in said envelope.

6. Apparatus for heating a person, comprising, in combination, a base, a heat source attached to said base, a flexible substantially tubular enclosure for receiving said person attached to said base so as to surround said heat source and said person, and at least one hoop secured to said enclosure so as to prevent said enclosure contacting said heat source.

7. Body warming apparatus for keeping a person warm comprising, in combination, a base having top and bottom surfaces, a heat source attached to said top base surface, a flexible substantially tubular enclosure having an open upper end and a bottom end attached to said base so as to surround said heat source, said enclosure being adapted for said person to stand on said base proximate said heat source and pull said enclosure up around the body of said person, a plurality of substantially concentric hoops attached to said enclosure so as to prevent said enclosure contacting said heat source and so as to permit air circulation around said person, a shield surrounding said heat source so as to prevent said person contacting said heat source, and means for securing said enclosure upper end to the body of said person so as to retain warm air in said enclosure around said person's body.

8. The body warming apparatus of claim 7 in which said enclosure upper end is secured to the body of said person by a pair of shoulder straps extending across the shoulders of said person.

9. The body warming apparatus of claim 7 in which said enclosure upper end is secured to said person by at least one shoulder strap having two ends that are each connected to said enclosure upper end and a drawstring in said enclosure upper end whereby said enclosure may be securely fastened to the body of said person by looping said shoulder strap across at least one shoulder and tying said drawstring so as to seal said enclosure upper end to the body of said person.

10. A body warmer for heating a person comprising, in combination, a base, a heat source secured to said base, a substantially tubular flexible envelope for receiving said body of said person, said envelope being attached to said base so as to permit said person to stand on said base proximate said heat source while substantially surrounded by said envelope, at least one hoop secured to said envelope so as to prevent said envelope from contacting said heat source, and a shield surrounding said heat source between said source and said person so as to prevent said person contacting said heat source.

11. Apparatus for warming a person's body comprising, in combination, a base having top and bottom surfaces and being substantially defined by a plane; an envelope having an upper end and a lower end that is secured to said base, said envelope being adapted to substantially surround the body of said person when said person stands on said base; a heat source secured to said base proximate said person when said person stands on said base in said envelope; at least one hoop secured to said envelope proximate said heat source for preventing said envelope from contacting said heat source and for permitting air circulation around said person in said envelope, said hoop having a circumference smaller than the circumference of said platform top surface so as to permit said envelope to be collapsed onto said platform top surface for storage; a shield substantially surrounding said heat source for preventing said person in said envelope from contacting said heat source; closure apparatus attached to said envelope upper end for supporting said envelope on said person in said envelope and for sealing said envelope to said person, said closure apparatus including shoulder straps for supporting said envelope on said person's shoulders when said person stands in said envelope, said closure apparatus also including a drawstring attached to said envelope upper end for selectively sealing said envelope upper end to the body of said person to permit adjusting the amount of air passing from inside the envelope to the atmosphere; a cover having top and bottom surfaces; a cushion attached to said cover bottom surface; means for attaching said cover to said base so as to seal said cushion, said heat source, said envelope, and said shield between said cover, said base, and said attachment means; a pivot mechanism for pivotally attaching said heat source and said shield to said platform top surface whereby said heat source and said shield may be pivoted from a first position in which they are placed for storage to a second position in which they are placed for use when said person is in said envelope; a latch mechanism for securely holding said heat source and said shield in said second position; and shoulder straps attached to said base bottom surface for carrying said body warmer when said base is attached to said cover.

* * * * *